United States Patent
Kammereck et al.

(10) Patent No.: US 6,857,224 B1
(45) Date of Patent: Feb. 22, 2005

(54) USE OF CLAY AND LIPID FORMULATIONS TO PROTECT HORTICULTURAL CROPS FROM SUNBURN AND INSECT DAMAGE

(75) Inventors: Rudolf Kammereck, Wenatchee, WA (US); Lawrence E. Schrader, Wenatchee, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/830,529

(22) PCT Filed: Oct. 26, 1999

(86) PCT No.: PCT/US99/25350
§ 371 (c)(1),
(2), (4) Date: Jul. 30, 2001

(87) PCT Pub. No.: WO00/24264
PCT Pub. Date: May 4, 2000

Related U.S. Application Data

(60) Provisional application No. 60/106,059, filed on Oct. 27, 1998.

(51) Int. Cl.$^7$ .......................... A01B 79/00; A01G 1/00; A01H 3/00
(52) U.S. Cl. ............... 47/58.1 FV; 47/24.1; 47/DIG. 6; 47/DIG. 11
(58) Field of Search .......................... 47/58.1 FV, 20.1, 47/24.1, DIG. 6, DIG. 11

(56) References Cited

U.S. PATENT DOCUMENTS

| | | | |
|---|---|---|---|
| 2,057,413 A | * | 10/1936 | Bridgeman et al. |
| 2,128,973 A | * | 9/1938 | Tisdale et al. |
| 2,198,991 A | * | 4/1940 | Dutton |
| 3,847,641 A | * | 11/1974 | Cushman et al. ............... 117/3 |
| 3,869,414 A | * | 3/1975 | Campbell ..................... 524/25 |
| 4,802,305 A | * | 2/1989 | Kojimoto et al. ............ 47/57.6 |
| 4,882,874 A | * | 11/1989 | Paulson et al. ................ 47/1.5 |
| 4,946,694 A | | 8/1990 | Gunnerson et al. |
| 5,049,186 A | | 9/1991 | Kawabata |
| 5,165,915 A | | 11/1992 | Tokubo et al. |
| 5,283,060 A | * | 2/1994 | Shieh .......................... 424/93 |
| 5,306,488 A | | 4/1994 | Vanlerberghe et al. |
| 5,733,531 A | * | 3/1998 | Mitchnick et al. ............. 424/59 |
| 5,908,708 A | | 6/1999 | Sekutowski et al. |
| 6,027,740 A | | 2/2000 | Puterka et al. |
| 6,036,765 A | * | 3/2000 | Farrow et al. ............... 106/487 |
| 6,069,112 A | | 5/2000 | Glenn et al. |
| 6,110,867 A | | 8/2000 | Glenn et al. |
| 6,156,327 A | | 12/2000 | Sekutowski et al. |
| 6,235,683 B1 | | 5/2001 | Glenn et al. |

FOREIGN PATENT DOCUMENTS

| | | | | |
|---|---|---|---|---|
| DE | 1492835 | * | 8/1965 | .......... A23G/00/00 |
| GB | 2011788 | * | 12/1978 | .......... A01N/17/00 |
| JP | 50-21382 | | 7/1990 | |
| WO | WO 98/38848 | | 9/1998 | |

\* cited by examiner

*Primary Examiner*—Peter M. Poon
*Assistant Examiner*—Andrea M. Valenti
(74) *Attorney, Agent, or Firm*—Christensen O'Connor Johnson Kindness PLLC

(57) ABSTRACT

Sunburn and insect damage to fruit and vegetable crops is significantly reduced by treatment of both fruit and foliage with a preventative amount of thixotropic smectic clay material, chemically altered to render its surface lipophilic, which is combined with a wax emulsion comprising a matrix of complex hydrocarbons, an emulsifying agent and water. In the practice of this invention the sunburn and insect protective composition is further diluted in an aqueous solution that is sprayable by commercial applicators.

34 Claims, No Drawings

USE OF CLAY AND LIPID FORMULATIONS TO PROTECT HORTICULTURAL CROPS FROM SUNBURN AND INSECT DAMAGE

CROSS-REFERENCE TO RELATED APPLICATION

This application claims the benefit of U.S. Provisional Application No. 60/106,059, filed Oct. 27, 1998.

FIELD OF THE INVENTION

The invention relates to protective coated fruits and vegetables, and methods for the treatment of plants that reduces the incidence of insect and sunburn damage.

BACKGROUND OF THE INVENTION

Sunburn has been a problem for apple growers for at least 75 years, but its incidence has increased in recent years with the widespread use of dwarfing rootstocks and high-density plantings. Many cultivars (e.g., 'Fuji,' 'Granny Smith,' 'Jonagold,' 'Gala,' and 'Braeburn') are susceptible to sunburn. Prominent growers have indicated that sunburn may be the most significant cullage or quality problem in the industry. Trees are smaller and fruit are more exposed to solar radiation making fruit more susceptible to sunburn.

There is no adequate product on the market today for preventing sunburn damage. Many growers use overhead evaporative cooling or shadecloth to reduce sunburn in their apple orchards. Evaporative cooling decreases the temperature of the fruit and helps protect the fruit from sunburn (Parchomchuk, P. and Meheriuk, M., "Orchard cooling With Pulsed Overtree Irrigation to Prevent Solar Injury and Improve Fruit Quality of 'Jonagold' Apples," *HortScience* 31:802–804 (1996)). However, growers are concerned about several deleterious effects on fruit trees and soil (Warner, G., "Overhead Cooling May Not Be Total Sunburn Cure," *Good Fruit Grower* 46(12):20–21 (1995)). The shadecloths cost several thousand dollars per acre to install, and frequently interfere with normal color development of fruit. Uniform shade causes an undesirable alteration in the growth habit of apple trees and significantly reduces fruit production (Warner, G., "Cooling Problems Prompt Growers To Try Covers," *Good Fruit Grower* 46(12):24–25 (1995); Warner, G., "Growers Test Shade Cloths To Reduce Fuji Sunburn," *Good Fruit Grower* 46(17):55–63 (1995); Warner, G., "What Shade Do Cloths Provide, What Do You Need?", *Good Fruit Grower* 46(17):50–53 (1995)). Problems with these approaches confirm that new treatments are needed to lower fruit temperature, but not interfere with color development or fruit production.

In 1986 and 1987, Sibbett et al. ("Effect Of A Topically Applied Whitener On Sun Damage To Granny Smith Apples," *California Agriculture* 45(1):9–10 (1991)) in California attempted to solve the problem by applying a commercial whitener (Sunguard) to Granny Smith apples. The whitener had been developed for walnuts. They concluded from their experiments that Granny Smith apples could not be protected from sunburn by up to four topical applications of this particular whitening agent.

Miller Chemical & Fertilizer Corp. (Hanover, Pa.) markets an anti-transpirant concentrate called VAPOR GARD, and claims in its advertisements that the product reduced sunburn cullage by 30% in their trials. Transpiration is important to plant leaves, as evapotranspiration serves to cool the leaves and protects the leaves from heating to temperatures that are deleterious. Fruits have much lower transpiration rates than do leaves, but it seems likely that applying an anti-transpirant to fruit would exacerbate a situation in which there is already too much thermal energy.

Myhob, Guindy, and Salem in Egypt (*Bulletin of Faculty of Agriculture*, University of Cairo, 47(3):457–469 (1996)) reported that Agricultural GatCool significantly reduced sunburn as compared to controls sprayed with water on Balady mandarin fruits. duToit in South Africa (*Citrus and Subtropical Fruit Research Institute Information Bulletin No.* 80:8–9 (1979)) reported that spraying Koolcote on pineapple trees decreased fruit flesh temperatures by 2–3 degrees Celsius.

Lipton and Matoba (*HortScience* 6(4):343–345 (1971)) reduced sunburn of 'Crenshaw' melons by whitewashing fruit with a suspension of aluminum silicate.

Ing (*Good Fruit Grower* 49(6):58 (1998)), commenting on unpublished field trials, reports that the application of kaolin to apple fruits not only acts as an insect repellent, but also lowers canopy temperature, increases fruit size, and may reduce sunburn. However, as noted by Ing, application of kaolin to fruit surfaces is problematic. To achieve an insecticidal result, large amounts of kaolin (50 to 100 pounds per acre) must be applied to the fruit trees. Current kaolin formulations are reported to suffer from substantial application problems such as excessive foaming and "globbing" in spray tanks. (*Good Fruit Grower* 49(6):58 (1998)). Furthermore, kaolin powders are easily washed off by rain, thus necessitating multiple applications in order to maintain beneficial effects. (*Good Fruit Grower* 49(6):58 (1998); see also *Washington State University Cooperative Extension Area Wide IPM Update* 3(4):1 (1998)).

Sekutowski et al. (U.S. Pat. No. 5,908,708) developed a protective water resistant coating that was formulated as an aqueous dispersion of particulate matter having a hydrophobic outer surface in a low boiling point organic liquid, such as methanol. The particulate matter of the Sekutowski et al. coating can be any finely divided hydrophobic particulate solids including minerals, such as calcium carbonate, mica, talc, kaolin, bentonites, clays attapulgite, pyrophyllite, wollastonite, silica, feldspar, sand, quartz, chalk, limestone, precipitated calcium carbonate, diatomaceous earth and barytes. One agricultural use of the Sekutowski et al. aqueous dispersions is to provide tree leaves with a water resistant coating by spraying the formulation onto the surface of the leaves. The water resistant coating is thought to reduce plant disease and insect damage. However, one major problem with the Sekutowski et al. formulation is the use of large volumes of organic liquids such as alcohols, ketones and cyclic ethers that are highly flammable and pose other health risks to workers during spray application.

Protective formulations which additionally function as pesticides in plant crops would be a valuable addition to Integrated Pest Management (IPM) practices providing "soft" suppression of pests without disrupting natural control processes. Desirable formulations would be expected to be non-toxic to mammals and thus safe for applicators and farm workers. Application of the protective formulations by commonly employed horticultural spray operations invariably involves treatment of foliage and fruit or vegetable. It is therefore important to develop new formulations that have protective properties against sunburn to fruits and vegetables as well as against damage caused by insects that inhabit both foliage and fruit.

In summary, there is a lack of adequate means to prevent sunburn and insect damage to fruit and vegetable crops. Thus, there is a strong need in agricultural markets for an inexpensive and effective composition that prevents sunburn, repels deleterious insects, is long lasting, and is relatively amenable to easy application by growers and commercial applicators.

SUMMARY OF THE INVENTION

It has now been discovered that the foregoing problems can be overcome and that sunburn in apples, and other fruit and vegetable crops requiring exposure to high intensity solar irradiance for maturation, can be significantly reduced by treating the crop with an effective amount of a plant protective coating composition of the present invention. An effective amount of a plant protective coating composition of the invention is defined as any amount of the inventive composition that upon application to the surface of a fruit or vegetable, results in the measurable reduction of the incidence of fruit or vegetable sun damage. The plant protective coating compositions of the invention also forms a barrier that reduces insect inflicted damage to the fruit or vegetable.

In one aspect, the present invention provides a fruit or vegetable that is protectively coated with a plant protective composition comprising lipophilic thixotropic smectic clay suspended in a wax emulsion. The wax emulsion preferably comprises complex hydrocarbons (also known as a matrix of hydrocarbons), at least one emulsifying agent and water. In a presently preferred embodiment of the present invention, both an anionic lipophilic hydrophilic emulsifier and a cation hydrophilic emulsifier are used to emulsify the matrix of hydrocarbons. Preferably, the protective composition is a mixture of about 0.5 to 10% (weight/weight) of lipophilic thixotropic smectic clay dispersed in about 90 to 99.5% (weight/weight) of the wax emulsion. For some uses of the inventive composition it is preferable to dilute the mixed composition into an aqueous solution. Preferably, the compositions of the invention are diluted into an aqueous solution in a volume/volume ratio of between about 1 part plant protective composition to about 1 part aqueous solution to about 1 part plant protective composition to about 10 parts aqueous solution.

Preferred plant protective coating compositions are sprayable onto fruit trees, vegetable crops and the like by a wide variety of commercial agricultural applicators. The matrix of hydrocarbons helps to maintain the physical integrity of the clay film on the fruit surface making the formulation more durable and resistant to rain wash. Because the plant protective coating compositions, when applied as finely dispersed spray particles, cover both foliage and fruit, a dual beneficial effect is achieved through prevention of the incidence of sunburn and damage by insects. The physical integrity of the clay film, as well as the matrix of hydrocarbons on foliage and fruit surfaces also provide an effective protective barrier against harmfill insects which may naturally reside on both foliage and fruit.

In the practice of the invention, proper dilution of the inventive composition in an aqueous solution allows effective spray application of the sun and insect protective material on to fruits or leaves prior to conditions that lead to the incidence of fruit sunburn or insect damage. The inventive composition is preferably sprayed onto plants at a rate of 100 to 500 gallons per acre. As compared to other formulations and treatments used to prevent sunburn damage of fruits, the inventive compositions and methods of application significantly reduce the incidence of fruit sunburn damage resulting in both fruit necrosis and browning.

The inventive compositions and methods are applicable to a wide variety of fruits and vegetables including, for example, apples, pears, tomatoes, peppers, curburbits, honeydew melons, cantaloupes, avocados, plums, beans, squashes, peaches, grapes, strawberries, raspberries, gooseberries, bananas, oranges, tulips, onions, cabbages, and other. See, for example, Brooks, C. and Fisher, D. F., "Some High-Temperature Effects in Apples: Contrasts in the Two Sides of an Apple," *J. Agr. Res.* 32(1):1–16. (1926); Ware, W. M., "High Temperature Injury on the Growing Apple," *Gardners Chron.* 92:287–288 (1932); Meyer, A., "Comparative Temperatures of Apples," *Proc. Amer. Soc. Hort. Sci.* 28:566567 (1932); Whittaker, E. C. and McDonald, S. L. D.,"Prevention of Sunscald of Deciduous Fruit Trees in Hot Climates," *Agr. Gaz. N. S. Wales* 52:231–233 (1941); Moore, M. H. and Rogers, W. S., "Sunscald of Fruits," *East Malling Res. Sta. Report, Pp.* 50–53. (1943); Cook, M. T., "Sunburn and Tomato Fruit Rots," *Phytopathologyy* 11:379–380 (1921); Harvey, R. B., "Sunscald of Tomatoes," *Minn. Studies Plant Sci.* 4:229–234 (1924); Harvey, R. B., "Conditions for Heat Canker and Sunscald in Plants," *J. Forestry* 23:292–294 (1925); Ramsey, G. B. and Link, G. K. K., "Market Diseases of Fruits and Vegetables: Tomatoes, Peppers and Eggplants," *U.S. Dept. Agr., Misc. Publ.* 121:28–29 (1932); Moore, M. H. and Rogers, W. S., "Sunscald of Fruits," *East Mailing Res. Sta. Report*, Pp. 50–53. (1943); Retig, N. and Kedar, N., "The Effect of Stage of Maturity on Heat Absorption and Sunscald of Detached Tomato Fruit," *Israel J. Agr. Res.* 17:77–83 (1967); Kedar, N. and Retig, N., "An Oblong Dwarf Tomato Resists Sunscald," *New Scientist* 36:546 (1967); Weber, G. F.,"Diseases of Peppers in Florida," *Florida Univ. Agr. Expt. Sta. Bull.* 244:35–37 (1932); Bremer, H., "On Pod Spots in Peppers," *Phytopathology* 35:283–287 (1945); Barber, H. N. and Sharpe, P. J. H., "Genetics and Physiology of Sunscald of Fruits," *Agr. Meterol* 8:178–191 (1971); Rabinowitch, H. D., Friedmann, M., and Ben-David, B., "Sunscald Damage in Attached and Detached Pepper and Cucumber Fruits at Various Stages of Maturity," *Scientia Hort.* 19:9–18 (1983); Rabinowitch, H. D., Ben-David, B., and Friedmann, M., "Light is Essential for Sunscald Induction in Cucumber and Pepper Fruits, Whereas Heat Conditioning Provides Protection," *Scientia Hort.* 29:21–29 (1986); Leclerg, E. L., "The Relation of Leaf Blight to Sun Scald of Honeydew Melons," *Phytopathology* 21:97–98 (1931); Lipton, W. J., "Ultraviolet Radiation as a Factor in Solar Injury and Vein Tract Browning of Cantaloupes," *J. Amer. Soc. Hort. Sci.* 102:32–36 (1977); Schroeder, C. A. and Kay, E., "Temperature Conditions and Tolerance of Avocado Fruit Tissue," *Calif. Avocado Soc. Yearbook* 45:87–92 (1961); Renquist, A. R., Hughes, H. G. and Rogoyski, M. K., "Solar Injury of Raspberry Fruit," *HortScience* 22:396–397 (1987); Maxie, E. C. and Claypool, L. L., "Heat Injury in Prunes," *Proc. Amer. Soc. Hort. Sci* 69:116–121 (1956); Farmer, A., "Sunscald of Japanese Plum Fruits," *Orchardist New Zealand* 51:113–114 (1968); Macmillan, H. G., "Sunscald of Beans," *J. Agr. Res.* 13:647–650 (1918); Macmillan, H. G., "Cause of Sunscald of Beans," *Phytopathology* 13:376–380 (1923); Macmillan, H. G. and Byars. L. P., "Heat Injury to Beans in Colorado," *Phytopathology* 10:365–367 (1920); Ramsey, G. B. and Wiant, J. S., "Market Diseases of Fruits and Vegetables: Asparagus, Onions, Beans, Peas, Carrots, Celery, and Related Vegetables," *U.S. Dept. Agr., Misc. Publ.* 440:17–32. (1941); Ramsey, G. B., Wiant, J. S. and Link., G. K. K., "Market Diseases of Fruits and Vegetables: Crucifers and Cucurbits," *U.S. Dept. Agr., Miscl Publ.* 292:20 (1938); Rhoads, A. S., "Sun-scald of Grapes and its Relation to Summer Pruning," *Amer. Fruit Grower* 44:2047 (1924);

Graves, A. H., "Sunscald of Tulip Flowers," *Phytopathology* 27:731–734 (1937); Green, G. C., "The Banana Plant. In: The Effect of Weather and Climate Upon the Keeping Quality of Fruit," *World Meteorological Organization, Technical Note No.* 53:113–135 Geneva (1963); Wade, N. L., Kavanagy, E. E. and Tan, S. C., "Sunscald and Ultraviolet Light Injury of Banana Fruits," *J. Hort. Science* 68:409–419 (1993); Ketchie, D. O. and Ballard, A. L., "Environments Which Cause Heat Injury to Valencia Oranges," *Proc. Amer. Soc. Hort. Sci.* 93:166–172. (1968). In addition, the plant protective compositions can be used on trees whose foliage is susceptible to sunburn, such as maples, basswood, boxelder, black walnut, birch, balsam fir, Douglas fir, Eastern white pine and spruce as well as many fruit trees (Litzow, M. and Pellett, H., "Materials for Potential use in Sunscald Prevention," *J. Arboriculture* 9:35–38 (1983); Green, S. B., "Forestry in Minnesota," *Geological and Natural History Survey of Minnesota, St. Paul* 401 pp. (1902); Huberman, M. A., "Sunscald of Eastern White Pine, *Pinus Strobus* L.," *Ecology* 24:456–471 (1943)). The inventive methods and compositions can also be used on plants that are not susceptible to sunburn but which are impacted by insect damage. In addition to the above listed plants that are susceptible to sunburn and insect damage, the following plants would independently benefit from the insect protective qualities of the inventive plant protective composition: soybeans, potatoes, peas, lentils, apricots, cherries.

DETAILED DESCRIPTION OF THE PREFERRED EMBODIMENT

Two types of sunburn exist in apples. One is a lethal phenomenon that leads to a necrotic area on the fruit. Such fruit becomes cullage. This phenomenon occurs when the sun-exposed side of apple skin reaches a temperature of 52°±1° Celsius for only 10 minutes. The second type of sunburn is a sublethal phenomenon that leads to a browning of the apple skin (sometimes referred to as "buckskin"). These apples can be sold, but at a lower grade and price.

Solar light contains ultraviolet, visible, and infrared radiation. All fruits and vegetables which develop a yellow or red coloration as part of their growth cycle require a certain quantity of ultraviolet and visible light to achieve the desired maturation color. Infrared light predominantly leads to excessive heating and associated damage to fruit surfaces. The plant protective compositions of the present invention selectively filter out the infrared portion of solar light but allow other light components to pass. The inventive clay coating is therefore invisible to the unaided eye. In contrast, kaolin based formulations appear on the surface of sprayed fruits and leaves as a whitish-gray dust, which uniformly reflects all components of solar light, therefore depriving the developing fruit of the beneficial aspects of solar light.

In one aspect, the present invention provides a fruit or vegetable that is protectively coated with a composition comprising lipophilic thixotropic smectic clay and a wax emulsion. The wax emulsion comprises a matrix of complex hydrocarbons, at least one emulsifier agent and water. Preferably, the wax emulsion contains two emulsifying agents: an anionic lipophilic emulsifier and an ionic hydrophilic emulsifier. Preferably, each emulsifier is present in the wax emulsion at a concentration of between 1–15% (weight/weight).

In another aspect, the present invention provides a method of protecting fruit and vegetables from sunburn, comprising treating a fruit or vegetable with a sunburn preventative amount of a plant protective composition comprising lipophilic thixotropic smectic clay and a wax emulsion. The wax emulsion is composed of a matrix of complex hydrocarbons, at least one emulsifier agent and water. Preferably, the composition is applied to the fruit or vegetable multiple times through the growing season.

In yet another embodiment of the invention a method of plant protection is provided, comprising treating a plant with an insect-controlling amount of a plant protective composition comprising lipophilic thixotropic smectic clay and a wax emulsion. The wax emulsion is composed of a matrix of complex hydrocarbons, at least one emulsifier agent and water.

The compositions and methods of the invention significantly decrease the incidence of both types of sunburn in apples. The plant protective compositions are preferably based on a thixotropic smectic clay material that is chemically altered to render its surface lipophilic. Thixotropic clays, in their original form are typically hydrophilic. In order to increase the ability of the protective compositions of the invention to adhere to the lipophilic surface of fruit, the clay is rendered lipophilic, such as, for example, by transformation by a chemical reaction of the clay with quaternary ammonium compounds in which the ligands consist entirely of aliphatic long-chain hydrocarbons or of a mixture of aliphatic and aromatic hydrocarbon residues. This reaction converts the hydrophilic clay into a hydrophobic and lipophilic material that is capable of molecularly dispersing oils, waxes and other lipid-like materials including organic solvents. Suitable thixotropic clay materials for use in the practice of the invention include clays that have been transformed by a chemical reaction of the clay with quaternary ammonium compounds and have a clay structure that weakens when subjected to shear forces and increases in strength upon standing. Many thixotropic smectic clays suitable for use in the practice of the present invention are commercially available through a variety of vendors.

As used herein, the term "smectic clay" material refers to a Bentonite, platelet-type clay. When transformed to render it lipophilic, this clay may also be referred to as "organoclay".

The successful functioning of the inventive sunburn protectant requires a matrix consisting of complex hydrocarbons which renders the formulation sprayable by commercial agricultural applicators, maintains the physical integrity of the clay on fruit and allows passage of visible solar radiation needed for fruit color formation but reflects undesired solar infrared light. The wax emulsion is formed by emulsifying natural or synthetic waxes with at least one emulsifying agent. Preferably, both an anionic lipophilic emulsifier and an ionic hydrophilic emulsifier are used to emulsify the matrix of hydrocarbons. The wax emulsion in the protective compositions of the present invention is intended to replace and enhance the properties of the natural wax layer which exists on the surface of all fruits and vegetables.

As used herein, the term "matrix of complex hydrocarbons" refers to a lipid based matrix that is capable of absorbing and dispersing the lipophilic organoclay. Suitable complex hydrocarbons for use in the present invention include, for example, natural and synthetic waxes that are suitable for human consumption, with melting temperatures that are higher than the melting temperatures of the target fruit or vegetable waxes. In a presently particularly preferred embodiment, the complex hydrocarbons of the present application is Carnauba Wax of a tropical origin. It contains a mixture of true waxes with long chain fatty acids and long chain esters. The fatty acid composition is complex but well represented by the term "Carnauba Wax" (*Corypha cerifera*). It will be apparent to those skilled in the art that other edible plant-derived waxes, such as Candelilla Wax (*Euphorbia cerifera* and *Pedilantus pavonis*), Alfa (*Stipa Tenacessima*), or mixtures thereof, will also be useful for this purpose. In addition, other natural wax mixtures well known in the art, such as montan wax, rice-bran wax, beeswax, Japan wax and mixtures thereof can also be used in the plant protective compositions of the present invention. It is also apparent that any edible synthetic waxes containing oxygen can also be used to practice the present invention. See, for example, the description of synthetic oxygen containing waxes in U.S. Pat. No. 5,049,186, incorporated herein by reference.

The wax emulsion of the present invention is made by emulsifying the matrix of hydrocarbons with an amount of an emulsifying agent sufficient to emulsify the matrix of hydrocarbons. In this regard, a large number of different emulsifier agents can be used to prepare the wax emulsion used in the practice of the present invention. See for example the emulsifying agents described in U.S. Pat. Nos. 5,049,186 and 5,165,915, incorporated herein by reference. Preferably, both an anionic lipophilic emulsifier and an ionic hydrophilic emulsifier are mixed with the matrix of hydrocarbons in an amount sufficient to emulsify the edible waxes. Preferably, the anionic lipophilic and the ionic hydrophilic emulsifiers are each present in the wax emulsion at a concentration of between about 1–15% (weight/weight) relative to the matrix of hydrocarbons.

The anionic lipophilic surfactants employed in the practice of the invention have, preferably, a hydrophilic-lipophilic balance (HLB) ranging from 10 to 40. They are principally salts of fatty acids (for example alkaline salts or organic salts such as amine salts), the said fatty acids having, for example, from 12 to 18 carbon atoms, and being able to have a double bond as in the case of oleic acid; the alkaline salts or salts of organic bases of alkyl-sulfuric and alkyl-sulfonic acids having 12 to 18 carbon atoms, of alkyl-arylsulfonic acids whose alkyl chain contains 6 to 16 carbon atoms, the aryl group being, for example, a phenyl group. They are also ether-sulfates, in particular, the sulfatation products of fatty alcohols and polyalkoxylated alkylphenols, in which the aliphatic chain has from 6 to 20 carbon atoms and the polyalkoxylated chain has from 1 to 30 oxyalkylene units, in particular oxyethylene, oxypropylene or oxybutylene. Preferred anionic hydrophilic surfactants are the fatty acids oleic acid and stearic acid.

Presently preferred ionic hydrophilic surfactants include amine compounds such as ethanolamine, diethanolamine, triethanolamine, alkyl alcohol amines such as methyl-ethanolamine, butyl-ethanolamine, morpholene and mixtures thereof.

The presently preferred wax emulsion for use as the wax emulsion in the plant protective coating composition of the present invention is APL-BRITE 310 C produced by Solutec Corporation (Yakima, Wash.). Other commercially available material suitable for use in the inventive protective coating composition are: Decco 231 produced by Elf-Atochem North America (Philadelphia, Pa.); Johnson's H.S and Johnson 31 produced by S.C. Johnson Wax (Racine, Wis.); and Shield Brite AP50C and Carnauba Gold produced by Pace International LLC (Seattle, Wash.).

A presently preferred material which meets the requirements specified for a chemically altered thixotropic smectic clay is Tixogel® MP 100 that can be commercially obtained from Süd-Chemie Rheologicals, a division of United Catalysts Inc. of Louisville, Ky. Tixogel® MP 100 is presently employed as an additive to a wide range of products including cosmetics, but not to our knowledge for any treatments of fruits or vegetables and not in combination with a matrix of complex hydrocarbons. A person with skill in the art will appreciate that many other organoclay materials having the required clay properties exist. Representative examples of useful clay materials include: numerous Tixogel and Optigel products, also produced by Süd-Chemie Rheologicals; the Bentone line of organoclays, obtainable from Rheox, Inc. (Highstown, N.J.); organoclays produced by Southern Clay Products (Gonzales, Tex.) and, the Vistrol and Organotrol lines of organoclays, sold by CIMBAR Performance Minerals (Cartersville, Ga.). The distinguishing property of the thixotropic organoclays used in the present invention is that they must be lipophilic.

For proper formulation of the inventive compositions it is essential to effect an activation of the organoclay (Tixogel® MP 100) with the wax emulsion (APL-BRITE 310 C) prior to dilution with water. A mixture of about 0.5 to 7% (weight/weight) Tixogel® MP 100 in APL-BRITE 310 C can be made at room temperature by mechanical stirring, but above about 7% (weight/weight) the mixture will quickly turn into a solid gel. Preferably, the plant protective composition is a mixture of about 5% (weight/weight) of Tixogel® MP 100 in about 95% (weight/weight) APL-BRITE 310 C. The resulting protective coating material contains thixotropic clay suspended in a sprayable wax emulsion. The ratio of thixotropic smectic clay to wax emulsion may change if products other than Tixogel® MP 100 or APL-BRITE 310C are employed as the organoclay and wax emulsion, respectively.

More generally, the plant protective composition of the present invention is a mixture of about 0.5 to 10% (weight/weight) lipophilic thixotropic smectic clay dispersed in about 90 to 99.5% (weight/weight) of the wax emulsion. Preferably, the plant protective composition is a mixture of about 3% to 7% (weight/weight) lipophilic thixotropic smectic clay dispersed in about 97 to 93% (weight/weight) of the wax emulsion. Most preferably, plant protective composition is a mixture of about 5% (weight/weight) lipophilic thixotropic smectic clay dispersed in about 95% (weight/weight) of the wax emulsion.

The wax emulsion comprises about 5% to 10% (weight/weight) natural wax or edible synthetic oxygen containing wax, about 2% to 30% (weight/weight) emulsifying agent and about 60 to 93% (weight/weight) water. Preferably, the emulsifying agent comprises about 1 to 15% (weight/weight) anionic lipophilic emulsifier, such oleic acid, and about 1 to 15% (weight/weight) ionic hydrophilic emulsifier, such as morpholene. When the anionic lipophilic emulsifier is oleic acid and the ionic hydrophilic emulsifier is morpholene, it is most preferable that morpholene be used at a molar ratio, relative to oleic acid, that is larger than about 1.0. Most preferably, the wax emulsion comprises about 5 to 10% (weight/weight) natural wax selected from the group consisting of Carnauba wax, Candelilla wax, Alfa wax, montan wax, rice-bran wax, beeswax, Japan wax and mixtures thereof, about 2 to 7% (weight/weight) oleic acid, about 2 to 7% (weight/weight) morpholene and about 76 to 91% (weight/weight) water.

The plant protective coating composition can be applied directly onto plants or it may be diluted in an aqueous solution in any ratio which accommodates the desired field spray technique. Suitable ratios for use of the present invention include, for example, dilution of the protective coating mixture into an aqueous solution in a volume/volume ratio of from about 1 part protective coating mixture to about 1 part aqueous solution to about 1 part protective coating mixture to 10 parts aqueous solution. In most applications for apple and pear fruit, the rate of spray volume ranges from 100 to 400 gal/acre. The number of spray applications per growing season is also variable but ranges from one application up to ten applications depending upon weather conditions. A person skilled in the art will appreciate that the above mentioned rates would be expected to change to a minimal degree if the inventive composition were applied to other fruits and vegetables, except that there would be a greater variation in final mixture/water ratios due to the specific requirements of agricultural crops involved, i.e. row crops, perennial trees, etc.

EXAMPLE 1

The beneficial effects of a representative protective composition of the invention in decreasing both types of sunburn in field trials on 'Jonagold' apples are shown in Table 1. The composition was 5% w/w of Tixogel® MP100 in APL-BRITE 310 C (hereafter PFT-X). PFT-X was applied at full strength onto apple fruits. A single application of the protectant was made to 'Jonagold' apples at Wenatchee, Wash. on Jul. 14, 1997. At the time of application no sunburn was observed on developing fruit. There was only one severe heat spell of sufficient intensity to cause the majority of sunburn during the 1997 season. It occurred during the first week of August. On August 19, apples treated with PFT-X had significantly less (P<0.05) sunburn necrosis and sunburn browning than did untreated control fruits. On September 10, sunburn necrosis was significantly lower in treated apples. The incidence of the necrosis type of sunburn was decreased by 66% on fruits treated with PFT-X in these field trials. The incidence of the surface browning type of sunburn ("buckskin") was decreased by 79%. Total sunburn was decreased by 73% in apples treated in accordance with the invention.

TABLE 1

Incidence of Sunburn Necrosis and Sunburn Browning as Influenced by PFT-X Formulation

| Fruit Variety | Observation Date | Incidence of Necrosis | | Incidence of Browning | |
| --- | --- | --- | --- | --- | --- |
| | | Control | Treated | Control | Treated |
| 'Jonagold' | 14 July 97 | 0[1] | 0 | 0 | 0 |
| | 29 July 97 | 6.7 | 5.0 | 6.7 | 0 |
| | 19 Aug. 97 | 26.3 | 9.1* | 17.5 | 3.6* |
| | 10 Sept. 97 | 25.9 | 8.8* | 6.9 | 0 |

[1]Each mean represents observations on 60 attached fruit that had been fully exposed to solar radiation for a daily duration of 3 hours before to 3 hours after solar noon. Controls received no application of the test formulation. Treated apples received one application of formulation.
*Denotes statistical significance of differences between control and treatment for each date as determined by a Yates-corrected z-test at the 0.05 level with n = 60.

EXAMPLE 2

The beneficial effects of a representative protective composition of the invention in decreasing sunburn in field trials on 5-year-old 'Jonagold' apples are shown in Table 2. The PFT-X composition was as listed in Table 1, but the formulation was diluted 1:1 with water before application to trees. Treatments were applied to single tree plots replicated ten times in a completely randomized design in the Clayton Orchard near Orondo, Wash. All treatments were applied with a handgun sprayer at approximately 150 pounds per square inch (psi) to near the point of drip, simulating a dilute spray of approximately 200 gallons/acre. For PFT-X, this provided 40 pounds of organoclay per acre and for Surround®, this provided 50 pounds of kaolin per acre. Each formulation was applied three times during the 1999 fruit growing season on July 7, August 4, and September 1. The control trees were sprayed with water on the same dates. For comparison, Surround®, a kaolin-based formulation containing proprietary surfactants and spreaders (marketed on a limited scale in 1999 by Engelhard Chemical Co., Iselin, N.J.) was applied in the same manner to another group of trees. Surrounds was formulated as suggested by the manufacturer using M-03, a proprietary Spreader/Sticker. 450 ml of M-03 was added to 50 lbs of kaolin clay (Engelhard Chemical M-97-009) that had previously been added to 100 gallons of water in a recirculating sprayer tank.

The sunburn data are presented in Table 2. The incidence of sunburn in all treatments was evaluated on August 31 by evaluating all fruit on each tree in the experiment. The percent of sunburn incidence for each tree was calculated. Both sunburn necrosis and sunburn browning were evaluated, but the incidence of sunburn necrosis was so low (<7% of total sunburn) that the two types were combined and analyzed statistically. Data were transformed using the angular or inverse sine transformation method (Steel and Torrie, Principles and Procedures of Statistics, McGraw-Hill Book Co., Inc., New York) prior to an analysis of variance.

TABLE 2

Incidence of Sunburn as Influenced by PFT-X.

Incidence of Sunburn (%)

| Fruit Variety | Control | Treated with PFT-X | Treated with Surround ® |
| --- | --- | --- | --- |
| 'Jonagold' | 15.77 | 6.01** | 15.26 |

**Denotes statistical significance of differences between control and PFT-X at the 0.01 level.
Total number of fruit evaluated were 723, 649, and 557 for the control, PFT-X treated, and Surround ®-treated apples, respectively.

The data in Table 2 indicate that apples treated in accordance with the invention showed significantly less sunburn than apples treated with water or Surround®.

EXAMPLE 3

The beneficial effects of a representative protective composition of the invention in decreasing sunburn in field trials on 3-year-old 'Cameo' apples are shown in Table 3. Sunburn damage was evaluated September 1. Other experimental details were the same as those in Example 2 except that trees were smaller, and two trees were included in each replication. The trees were in the Fleming Orchard near Orondo, Wash.

TABLE 3

Incidence of sunburn as influenced by PFT-X Application

Incidence of Sunburn (%)

| Fruit Variety | Control | Treated with PFT-X | Treated with Surround ® |
| --- | --- | --- | --- |
| 'Cameo' | 13.40 | 6.59** | 13.85 |

**Denotes statistical significance of differences between control and PFT-X at the 0.01 level.
Total number of fruit evaluated were 291, 260, and 258 for the control, PFT-X treated, and Surround ®-treated apples, respectively.

The incidence of sunburn in 'Cameo' apples was reduced significantly when treated with the inventive PFT-X formulation as compared to apples treated with water or Surround® (Table 3).

EXAMPLE 4

The beneficial effects of a representative protective composition of the invention in decreasing sunburn in field trials on 9-year-old 'Fuji' apples are shown in Table 4. Sunburn damage was evaluated October 19. Other experimental details were the same as those in Example 2 except that a fourth application of formulations was made September 29. All fruit on two large branches of each tree were evaluated, as trees were much larger than those used in Examples 2 and 3. The trees were in the Fugachee Orchards near Pateros, Wash.

TABLE 4

Incidence of sunburn as influenced by PFT-X Application

| | Incidence of Sunburn (%) | | |
|---|---|---|---|
| Fruit Variety | Control | Treated with PFT-X | Treated with Surround ® |
| 'Fuji' | 14.85 | 2.44** | 8.59 |

**Denotes statistical significance between PFT-X and both control and Surround ® at the 0.01 level.
Total number of fruit evaluated were 485, 779, and 489 for the control, PFT-X treated, and Surround ®-treated apples, respectively.

The incidence of sunburn in 'Fuji' apples was reduced significantly when treated with the inventive PFT-X formulation as compared to apples treated with water or Surround® (Table 4).

EXAMPLE 5

To evaluate the entomological efficacy of the inventive formulation PFT-X, a trial was conducted with 12-year-old 'Gala' apple trees at the Washington State University Tree Fruit Research & Extension Center, Wenatchee, Wash. Control of codling moth (*Cydia pomonella* L.)(CM) during their second generation was evaluated. PFT-X treatments were applied to single tree plots replicated five times in a randomized complete block. PFT-X was applied with a hand-gun sprayer at 300 psi to the point of drip, simulating a dilute spray of approximately 400 gallons/acre. Three different PFT-X and Surround® application protocols were tested:

1) trees were sprayed with PFT-X or Surround® three times during the CM oviposition period (Jul. 19 [1,000 degree day total], Jul. 27 and Aug. 4, 1999);

2) trees were sprayed with PFT-X or Surround® three times during the CM hatch period (August 12 [1,250 degree day total], August 18 and 25); and 3) trees were sprayed with PFT-X or Surround® six times (all dates) covering the CM oviposition and hatch periods. For all PFT-X and Surround® application protocols a sample of fruits was harvested and an evaluation of CM insect damage to the fruit was made on September 1 by visually inspecting fifty apples per replicate and recording the number of stings and entries.

TABLE 5

Codling Moth damage to apple fruit as influenced by applications of PFT-X or Surround ® during oviposition, hatch, or oviposition + hatch.

| | Rate | | #/50 fruit | | |
|---|---|---|---|---|---|
| Treatment | (Form./ 100 gal | Timing[1] | Stings | Entries | % total injury |
| Surround ® | 25 lbs | Oviposition | 0.8a[2] | 3.0bc | 7.6b |
| Surround ® | 25 lbs | Hatch | 0.8a | 4.0b | 9.6b |
| Surround ® | 25 lbs | Oviposition + hatch | 0.8a | 2.0bc | 5.6b |
| PFT-X | 20 lbs | Oviposition | 0.8a | 2.6bc | 6.8b |
| PFT-X | 20 lbs | Hatch | 1.2a | 2.2bc | 5.2b |
| PFT-X | 20 lbs | Oviposition + hatch | 1.4a | 0.2c | 3.2b |
| Untreated | NONE | | 0.8a | 12.2a | 26.0a |

[1]Application dates for Oviposition timing were July 19, July 27 and Aug. 4 and for the Hatch timing were Aug. 12, 18, and 25. Applications for the Oviposition + hatch timing included all six dates.
[2]Means in the same column followed by the same letter not significantly different (P = 0.05, Duncan's new multiple range test).

Both the PFT-X and Surround® treatments significantly reduced CM injury relative to the untreated control (Table 5). There was no difference in the number of CM stings (shallow unsuccessful entries) across treatments. Most of the effect of the treatments with both PFT-X and with Surround® was observed in the reduction of successful entries into fruit. There was no observed advantage of timing, but when applications were made to both the oviposition and hatch periods, the level of fruit injury was slightly lower than when treatments were applied to either the oviposition or hatch period. The formulations of the present invention show promise as tools to manage codling moth, probably as supplements to other "soft" tactics such as mating disruption. These data and the data presented in Tables 1–4 demonstrate that the inventive composition has dual benefits when applied to fruit trees. The inventive composition is effective at significantly reducing the incidence of fruit sunburn and reducing fruit damage caused by codling moth.

EXAMPLE 6

Some formulations cause phytotoxicity and others affect physiological processes such as photosynthesis when applied to trees. It has been shown that any unusual change in the overall bioenergetic status of the plant can be detected by a change in chlorophyll fluorescence (See generally, Lichtenthaler, K. K., "Applications of Chlorophyll Fluorescence in Photosynthesis Research, Stress Physiology," *Hydrobiology and Remote Sensing*, Kluwer Academic Publishers, Dordrecht, Germany (1988)). This includes all the reactions from the oxidation of water through electron transport, development of the electrochemical gradient, ATP synthesis, and eventually the series of enzymatic reactions for $CO_2$ reduction to carbohydrate in the leaf. Even changes in the plant that affect stoma opening and gas exchange with the atmosphere are reflected by changes in the fluorescence characteristics of a leaf. Therefore fluorescence was used as an indicator of any deleterious effects resulting from application of formulation. An OS5-FL Modulated Chlorophyll Fluorometer (Opti-Sciences, Inc. Tyngsboro, Mass.) was used to determine 'dark-adapted' Fv/Fm. $Fv/Fm = Fm-Fo/Fm$ where Fo and Fm are the minimal and maximal fluorescence yield of a 'dark adapted' sample. Fluorescence was determined on five attached leaves on trees in each of the five replications used in Example 4. On average, 84% of the incident quanta are absorbed by a leaf. Thus, a value for Fv/Fm of about 0.8 indicates healthy leaves with near maximal electron transport.

TABLE 6

Influence of PFT-X and Surround ® on fluorescence of leaves (estimation of electron flow in Photosystem II of photosynthesis). Same trees and treatments used in Example 4 were tested.

| Treatment | Rate of (Form./ 100 gal) | Application Dates | Fluorescence (Fv/Fm) |
|---|---|---|---|
| Surround ® | 25 lbs | July 19, July 27, Aug. 4 | 0.777 |
| Surround ® | 25 lbs | Aug. 12, 18, and 25 | 0.797 |
| Surround ® | 25 lbs | July 19, 27; Aug. 4, 12, 18, 25 | 0.816 |
| PFT-X | 20 lbs | July 19, July 27, Aug. 4 | 0.808 |
| PFT-X | 20 lbs | Aug. 12, 18, and 25 | 0.781 |
| PFT-X | 20 lbs | July 19, 27; Aug. 4, 12, 18, 25 | 0.785 |
| Untreated | NONE | | 0.801 |

The results in Table 6 indicate that the inventive formulation had no significant effect on (P=0.05) fluorescence of the leaves to which formulation was applied. Thus, no evidence of damage to the overall bioenergetic status of the trees is seen with any of the formulations. No phytotoxicity to either fruit or leaves was observed with any formulations.

EXAMPLE 7

Before field testing, entomologists sometimes conduct bioassays to determine the inherent toxicity of new formulations, changes in behavior of insects exposed to new formulations, and appropriate concentrations to apply. Accordingly, the inventive PFT-X formulation was used in two bioassays.

Adulticide bean disk bioassay. Leaf disks (2 cm diameter) were cut from untreated leaves of bean (*Phaseolus vulgaris* 'Henderson Bush'). Disks were floated with the abaxial (lower) surface up in a ¾ ounce plastic portion cup filled with cotton and distilled water. Twenty adult twospotted spider mites (TSM), (*Tetranychus urticae* Koch) were transferred to the lower surface with a fine paintbrush. The leaf disks containing mites were treated with five concentrations of PFT-X or a distilled water check.

All cups containing the five replicates of each treatment were treated at the same time in a Potter Spray Tower equipped with the intermediate nozzle, and set to 6.5 psi. Two ml of the pesticide solution were placed in the reservoir, and sprayed onto the disks. The mites were held in a growth chamber at 22±2° C. Mites were evaluated variously from 24 h after treatment for response as described immediately below.

| Category | Description |
|---|---|
| Alive | Moving without stimulation, or capable of moving >1 body length after gentle stimulation with brush. |
| Dead | No movement whatsoever, even after stimulation; or desiccated. |
| Moribund | Capable of producing some movement, especially twitching of legs, but unable to move >1 body length after stimulation. |
| Runoff | Found in cotton or water surrounding leaf surface, but not on leaf disk. Makes no difference if dead or alive. (If walk off occurs during the course of the evaluation, count as alive.) |

Table 7 presents the results obtained using the bean disk bioassay and PFT-X at a variety of application doses.

TABLE 7

Mortality and runoff resulting from treatment of twospotted spider mites on bean disks treated with PFT-X. PFT-X was applied June 29, 1999, and the evaluation was done June 30. The full-strength PFT-X as described in Table 1 was diluted in distilled water to provide concentrations ranging from 100 to 700 grams of PFT-X per liter.

| Concentration (g/liter) | No. Subjects | % Mortality | % Runoff |
|---|---|---|---|
| 700 | 111 | 7.3 | 1.0 |
| 500 | 103 | 3.8 | 3.5 |
| 300 | 99 | 0.0 | 4.6 |
| 200 | 101 | 2.9 | 1.9 |
| 100 | 102 | 4.9 | 0.0 |
| 0 | 103 | 4.5 | 4.6 |

The results in Table 7 indicate that there was no dose response to the inventive PFT-X formulation after 24 h, either in terms of mortality or runoff.

Motile Stage Mortality and Behavior, Whole Plant Bioassay: Five leaves on each of six infested bean plants from the 1998 composite TSM colony were tagged. Prior to treatment, all motile stages were counted with a 5x-magnification headband (OptiVisor). Counts from the top and bottom side of the leaf were recorded separately. The same leaves were counted 24 h after treatment. Various concentrations of PFT-X were applied with a hand-pump-pressurized sprayer. The suspensions were kept under constant agitation during application. Five replicates were used for each treatment. Table 8 shows the data obtained from the whole plant bioassays with the inventive PFT-X formulation applied at a variety of concentrations. Primary data were analyzed using the General Linear Models Procedure of SAS (SAS 1988 (*Statistical Analysis Institute*, 1988; *SAS/Stat User's Guide*, Release 6.03 Edition; SAS Institute, Inc., Cary, N.C.)) using both a classification model (AOV) and numeric (regression).

TABLE 8

Location and mortality status of mites before and after treatment with the inventive formulation in a whole bean plant bioassay. PFT-X was diluted as described in Table 7, and applied June 30, 1999. Pre-treatment observations were made before application on June 30, and post-treatment observations were made on July 1, 1999. Means in the same column followed by the same letter not significantly different.

| | Live | | | | Dead | |
|---|---|---|---|---|---|---|
| Concn in g/liter | Total live mites/ leaf | Total surface mites/ leaf | Bottom surface mites/ leaf | Top surface % mites | Top surface mites/ leaf | Bottom surface mites/ leaf |
| Pretreatment | | | | | | |
| 700 | 35.6a | 5.8a | 29.8a | 17.2 | — | — |
| 500 | 33.6a | 4.8a | 28.8a | 15.9 | — | — |
| 300 | 35.8a | 8.4a | 27.4a | 22.2 | — | — |
| 200 | 35.6a | 8.0a | 27.6a | 23.6 | — | — |
| 100 | 38.2a | 9.8a | 28.4a | 30.4 | — | — |
| 0 | 29.0a | 12.6a | 16.4a | 42.9 | — | — |
| Post-treatment | | | | | | |
| 700 | 7.2a | 2.4a | 4.8a | 28.7 | 3.8 | 3.8 |
| 500 | 11.4a | 3.8a | 7.6a | 36.4 | 2.2 | 4.0 |
| 300 | 6.8a | 1.8a | 5.0a | 25.0 | 4.0 | 4.2 |
| 200 | 14.6a | 4.2a | 10.4a | 27.7 | 2.8 | 2.4 |
| 100 | 12.2a | 3.2a | 9.0a | 22.5 | 2.6 | 5.4 |
| 0 | 14.0a | 6.6a | 7.4a | 42.6 | 4.8 | 3.6 |

Although there was a considerable decrease in mite population after treatment with PFT-X, this decrease was not related to concentration. No differences among the various concentrations of PFT-X occurred in any of the variables measured or calculated (Table 8). In addition to mortality, the behavior of the mites (i.e., occupation of the upper versus lower surface of the leaf) was observed. Normally, the TSM preferentially occupy the lower leaf surface, and most of the webbing is found there. Treatment with the PFT-X did not alter this pattern (Table 8). The relationship between concentration and percentage occupancy on the upper leaf surface was analyzed by regression analyses, but no significant relationship existed after the treatment (data not shown). In summary, PFT-X does not appear to affect either mortality or one aspect of behavior (leaf surface preference) of these mites.

EXAMPLE 8

The effects of the inventive formulation (PFT-X) on phytophagous mites and their natural enemies were examined in an apple orchard. Four-year-old 'Oregon Spur Delicious' apples were used. Treatments were applied with an air-blast sprayer calibrated to deliver 100 gallons per acre. PFT-X treatments were applied Aug. 4, 1999. The plot originally had no mite populations, so the orchard was seeded with twospotted mites (*Tetranychus urticae* Koch) from a greenhouse colony and later with European red mites (*Panonychus ulmi* Koch) from another orchard. In addition, the plot was sprayed with Asana® 0.66EC (DuPont Co., Wilmington, Del.)(1 pint/acre) plus Lorsban® 50W (Dow Chemical, Midland, Mich.)(3 lbs/acre) to reduce codling moth populations in the plots. Post-treatment mite counts were taken every week until early fall. A sample of 20 leaves per plot was taken and kept cool during transportation to the laboratory. Mites were removed from the leaves with a leaf-brushing machine, and collected on a revolving sticky glass plate. Mites on the plate were counted with the aid of a stereoscopic microscope. Motile and egg stages of the pest mites European red mite, twospotted spider mite, and McDaniel spider mite (*Tetranychus mcdanieli* McGregor) were counted, along with motile and egg stages of the predatory mites *Typhlodromus occidentalis* (Nesbitt) and *Zetzellia mali* (Ewing). Motile stages only of apple rust mite, *Aculus schlechtendali* (Nalepa), were also counted. The eggs of twospotted spider mite and McDaniel mite could not be distinguished from one another, and were recorded as a single category (*Tetranychus* eggs).

Table 9 presents the phytophagous and predatory mite population data and the effects of spray applications of various formulations including the inventive PFT-X composition.

TABLE 9

Phytophagous and predatory mite populations before and after treatment with miticides and formulations.

| Treatment | Rate/acre | Aug. 2 | Aug. 11 | Aug. 17 |
|---|---|---|---|---|
| | | Total tetranychids/leaf | | |
| PFT-X | 10 lbs. | 6.99a[1] | 6.92a | 20.51a |
| PFT-X | 20 lbs. | 7.75a | 9.95a | 10.04a |
| Surround ® | 25 lbs. | 6.74a | 23.01a | 19.24a |
| Surround ® | 50 lbs. | 13.51a | 8.91a | 22.13a |
| Orchex 796[2] | 1% | 9.09a | 21.25a | 6.70a |
| Pyramite ® 60W[3] + Orchex 796 | 4.4 oz.+ 0.25% | 8.14a | 5.83a | 11.89a |
| Check | — | 7.16a | 13.93a | 29.98a |

TABLE 9-continued

Phytophagous and predatory mite populations before and after treatment with miticides and formulations.

| Treatment | Rate/acre | Aug. 2 | Aug. 11 | Aug. 17 |
|---|---|---|---|---|
| | | Total predatory mites/leaf | | |
| PFT-X | 10 lbs. | 0.13a | 0.13a | 1.30a |
| PFT-X | 20 lbs. | 0.00a | 3.59a | 0.00a |
| Surround ® | 25 lbs. | 0.10a | 3.43a | 0.29a |
| Surround ® | 50 lbs. | 0.00a | 0.04a | 0.38a |
| Orchex 796 | 1% | 0.00a | 0.79a | 0.75a |
| Pyramite ® 60W + Orchex 796 | 4.4 oz.+ 0.25% | 0.03a | 1.04a | 0.09a |
| Check | — | 0.18a | 0.09a | 0.33a |

[1]Data were analyzed using analysis of variance on each count date (PROC GLM; SAS Institute, 1988). Means were separated with the Waller-Duncan k-ratio t-test.
[2]Purchased from Exxon Company, U.S.A., Houston, TX.
[3]Purchased from BASF Agriculture Products, Research Triangle Park, NC.

The mite populations consisted primarily of twospotted mites (71% overall) with some European red mite, and occasionally, some McDaniel mite forming a proportion of the population. The predatory mite population was primarily *T. occidentalis* (82% overall), with the remainder of the population comprised of *Z. mali*. Populations began to rise in late July, and were at an appropriate level (3 to 8 mites/leaf) by early August. No statistical differences occurred among any of the treatments (including the untreated check) at any time during the course of the experiment, despite treatment means that ranged from 7 to 30 mites/leaf (Table 9).

Predatory mite populations were high but variable throughout the test. On the first post-treatment count date (August 11), the low rate of Surround® and the high rate of PFT-X had exceptionally high *T. occidentalis* populations (Table 9). This is especially notable since Asana®, a chemical known for its toxicity to predatory mites, was being sprayed at intervals. The use of Asana® compromised the test for predator toxicity, but there was no evidence that any of the materials were acutely toxic to *T. occidentalis* and *Z. mali*.

An additional mite control variable, known as cumulative mite days (CMD) was calculated for the formulations indicated in Table 9. CMD was calculated for each formulation using the equation:

$$CMD = \Sigma 0.5(pop_1 + pop_2)(date_1 - date_2),$$

where $pop_1$ is the population (total tetranychids/leaf) on $date_1$ and $pop_2$ is the population (total tetranychids/leaf on $date_2$).

CMD represents a time-weighted measurement of the populations. The CMD for Pyramite®+Orchex (CMD=402) was lowest. The CMD was 423 for PFT-X (10 lbs./A), and 477 for PFT-X (20 lbs./A). The CMD for the check was 567. The CMD was 508 for Surrounds (50 lbs./A) and 519 for Surround® (25 lbs./A). For Orchex 796, the CMD was 513. The CMD data above indicate that PFT-X seemed to provide some suppression of the leaf mite populations across the growing season.

In summary, the inventive formulation of PFT-X tested in Table 9 had no apparent toxicity on the mites or their predators. As expected, PFT-X did not cause mortality in the mites. However, it is particularly important that the inventive formulation does not kill the beneficial predators or repel them from the leaf's surface, as this result indicates that PFT-X will be useful in Integrated Pest Management (IPM). In IPM practices, a formulation is useful only if the formulation provides what is called "soft suppression" of pests. That is, the IPM formulation does not cause a significant disruption to the natural control processes by, for example, negatively impacting populations of beneficial organisms.

EXAMPLE 9

The effects of several formulations on leafhopper nymphs in an apple orchard (cv. 'Braeburn') near Quincy, Wash. were examined. Four replicates were used where each replicate consisted of three trees in a single row. Leafhopper nymphs were sampled by counting the nymphs on 20 leaves/tree. Populations were sampled weekly until the majority of the population had transformed to the adult stage. A single-spray program and a three-spray program were compared. The single-spray treatment and the first application of the three-spray program were applied on Aug. 3, 1999, using a multiple tank air-blast sprayer calibrated to deliver 100 gallons/acre. The second and third sprays of the three-spray program were applied on Aug. 12 and Aug. 20, 1999. Table 10 presents the data obtained from this study.

EXAMPLE 10

The beneficial effects of a representative protective composition of the invention in decreasing damage by deleterious insects to foliage and fruit is tested in field trials on (A) apples [cv. 'Delicious', 'Golden Delicious', 'Fuji', 'Cameo', 'Jonagold' and 'Gala'] with the following target insects: codling moth, leafrollers, leafhoppers, spider mites, aphids, leafminers, true bugs (*Pentatomidae* and *Miridae*), cutworms, fruit worms, apple maggot, cherry fruit fly and San Jose scale; and on (B) pears [cv. 'Bartlett' and 'd'Anjou'] with the following target insects: pear psylla, true bugs, cutworms, spider mites, mealybug, and codling moth. Initial tests are conducted with high-pressure handgun spray equipment using a spray volume equivalent to 100 to 400 gal/acre. The results obtained allow determination of an activity profile for the inventive formulation on the target insects. Increasing concentrations of Tixogel® MP100 from 1 to 5% in APL-BRITE 310 C are used with aqueous dilutions of ½ to 1/10 strength to arrive at appropriate concentrations. Treatments are replicated three to six times in a randomized complete block design with single trees or small blocks of trees. An appropriate control consists of trees that receive no spray treatments. For entomological evaluations of pests on foliage, populations of insects such as

TABLE 10

Leafhopper nymph populations before and after treatment with pesticides and formulations.

| Treatment | Rate/acre | No. appl. | July 29 | Aug 6 | Aug 9 | Aug 16 | Aug 23 | Aug 31 |
|---|---|---|---|---|---|---|---|---|
| | | | | Leafhopper nymphs/leaf | | | | |
| PFT-X | 20 lbs | 1 | 3.89a[1] | 1.99bcd | 0.91c | 3.86abc | 3.55ab | 1.10ab |
| PFT-X | 20 lbs | 3 | 3.54a | 2.81bc | 2.85a | 3.49abc | 3.40ab | 1.21ab |
| Surround ® | 50 lbs | 1 | 3.44a | 1.86bcd | 1.09bc | 2.38bc | 2.63ab | 1.36a |
| Surround ® | 50 lbs | 3 | 3.49a | 1.41cd | 1.08c | 1.88c | 2.01bc | 0.31b |
| Orchex 796 | 1% | 1 | 3.44a | 3.28b | 3.36a | 5.01ab | 4.15a | 1.65a |
| Pyramite ® 60W + Orchex 796 | 4.4 oz + 0.25% | 1 | 3.53a | 1.34cd | 2.46ab | 5.09ab | 3.73ab | 1.44a |
| Provado ® L6F[2] + Sylgard 309[3] | 6 fl oz + 4 fl oz. | 1 | 3.70a | 0.61d | 0.20c | 1.18c | 0.60c | 0.94ab |
| Check | — | — | 3.70a | 6.11a | 3.79a | 6.28a | 4.24a | 1.85a |

[1]Data were analyzed using analysis of variance on each count date (PROC GLM; SAS Institute, 1988). Means were separated with the Waller-Duncan k-ratio t-test. Means within columns not followed by the same letters are significantly different.
[2]Purchased from Bayer Corporation, Pittsburgh, PA.
[3]Purchased from Wilfarm, L.L.C., Gladstone, MO.

The inventive PFT-X formulation (single application on August 3) provided suppression of nymphs through August 9, but thereafter the population mean was not different from the check (Table 10). With the three-spray program, PFT-X significantly suppressed nymph populations only on August 6, although the population means for the nymphs were always lower than the check. Only the standard (Provado+Sylgard) provided much knockdown and residual control.

Orchex 796, an oil used by some in IPM programs as a soft pesticide, was included in this test. It was different than the check only on August 6. Its suppression of nymph populations was therefore much like that of the inventive PFT-X formulation. Thus, the data presented in Table 10 indicate that the PFT-X formulation of the present invention can be used as a component of an integrated pest management program.

mites, aphids, leafhoppers, pear psylla, and leafminers are evaluated pre-treatment and at intervals in the post-treatment period to determine efficacy. For pear psylla and other pests such as the codling moth, scale, and leafrollers, the level of injury to fruit is evaluated at three times during the growing season in each treatment by checking at least 25 fruit per tree (replicate).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A fruit or vegetable coated with a plant protective coating comprising lipophilic thixotropic smectic clay and a wax emulsion, wherein the wax emulsion comprises a matrix of complex hydrocarbons, an anionic lipophilic emulsifier, an ionic hydrophilic emulsifier and water, wherein the anionic lipophilic emulsifier is selected from the group consisting of oleic acid, stearic acid and mixtures thereof, wherein the ionic hydrophilic emulsifier is selected from the group consisting of ethanolamine, diethanolamine, triethanolamine, alkyl alcohol amine, morpholene and mixtures thereof.

2. The fruit or vegetable of claim 1 wherein the wax emulsion comprises an edible synthetic oxygen containing wax.

3. The fruit or vegetable of claim 1 wherein the plant protective coating comprises about 0.5 to 10% (weight/weight) lipophilic thixotropic smectic clay and about 90 to 99.5% wax emulsion.

4. The fruit or vegetable of claim 3 wherein the protective coating mixture is diluted into an aqueous solution in a volume/volume ratio of from about 1 part protective coating mixture to about 1 part aqueous solution to about 1 part protective coating mixture to 10 parts aqueous solution.

5. The fruit or vegetable of claim 1 wherein the matrix of complex hydrocarbons comprises a wax mixture comprising long chain fatty acids and long chain esters.

6. The fruit or vegetable of claim 5 wherein the wax mixture is a natural wax selected from the group consisting of Carnauba wax, Candelilla wax, Alfa wax, montan wax, rice-bran wax, beeswax, Japan wax and mixtures thereof.

7. The fruit or vegetable of claim 1 wherein the fruit or vegetable is an apple.

8. A plant protective composition comprising:
about 0.5 to 10% (weight/weight) lipophilic thixotrophic smectic clay, and
about 90 to 99.5% (weight/weight) wax emulsion, said emulsion comprising:
about 5 to 10% (weight/weight) natural wax selected from the group consisting of Carnauba wax, Candelilla wax, Alfa wax, montan wax, rice-bran wax, beeswax, Japan wax and mixtures thereof;
about 1 to 15% (weight/weight) oleic acid;
about 1 to 15% (weight/weight) morpholene; and
about 60 to 93% water.

9. A fruit or vegetable coated with the plant protective composition of claim 8.

10. The fruit or vegetable of claim 9 wherein the fruit or vegetable is an apple.

11. A method of protecting a plant from sunburn, comprising treating said plant with a sunburn preventative amount of a plant protective composition comprising lipophilic thixotropic smectic clay and a wax emulsion, wherein the wax emulsion comprises a matrix of complex hydrocarbons, an anionic lipophilic emulsifier, an ionic hydrophilic emulsifier and water, wherein the anionic lipophilic surfactant is selected from the group consisting of oleic acid, stearic acid and mixtures thereof, wherein the ionic hydrophilic emulsifier is selected from the group consisting of ethanolamine, diethanolamine, triethanolamine, alkyl alcohol amine, morpholene and mixtures thereof.

12. The method of claim 11 wherein the treated plant is selected from the group consisting of apple, pear, tomato, pepper, curburbit, honeydew melon, cantaloupe, avocado, plum, bean, squash, peach, grape, strawberry, raspberry, gooseberry, banana, orange, tulip, onion, cabbage, maple tree, basswood tree, boxelder tree, black walnut tree, birch tree, balsam fir, Douglas fir, Eastern white pine and spruce.

13. The method of claim 12 wherein the treated plant is an apple.

14. The method of claim 11 wherein the wax emulsion comprises an edible synthetic oxygen containing wax.

15. The method of claim 11 wherein the plant protective composition comprises about 0.5 to 10% (weight/weight) lipophilic thixotropic smectic clay and about 90 to 99.5% of the wax emulsion.

16. The method of claim 15 wherein the plant protective composition is diluted into an aqueous solution in a volume/volume ratio of from about 1 part protective coating mixture to about 1 part aqueous solution to about 1 part protective coating mixture to 10 parts aqueous solution.

17. The method of claim 11 wherein the matrix of complex hydrocarbons comprises a wax mixture comprising long chain fatty acids and long chain fatty alcohol esters.

18. The method of claim 17 wherein the wax mixture is a natural wax selected from the group consisting of Carnauba wax, Candelilla wax, Alfa wax, montan wax, rice-bran wax, beeswax, Japan wax and mixtures thereof.

19. The method of claim 11 wherein the plant protective composition is diluted into an aqueous solution prior to treating the plant.

20. The method of claim 11 wherein the plant is treated by spraying the composition onto the surface of the plant.

21. The method of claim 20 wherein the composition is sprayed with an application rate of about 100 to 500 gallons per acre.

22. The method of claim 20 wherein the composition is sprayed onto the plant multiple times.

23. A method of protecting a plant from insect damage comprising treating a plant with an insect-controlling amount of a plant protective composition comprising lipophilic thixotropic smectic clay and a wax emulsion, wherein the wax emulsion comprises a matrix of complex hydrocarbons, an anionic lipophilic emulsifier, an ionic hydrophilic emulsifier and water, wherein the anionic lipophilic surfactant is selected from the group consisting of oleic acid, stearic acid and mixtures thereof, wherein the ionic hydrophilic emulsifier is selected from the group consisting of ethanolamine, diethanolamine, triethanolamine, alkyl alcohol amine, morpholene and mixtures thereof.

24. The method of claim 23 wherein the treated plant is selected from the group consisting of apple, pear, tomato, pepper, curburbit, honeydew melon, cantaloupe, avocado, plum, bean, squash, peach, grape, strawberry, raspberry, gooseberry, banana, orange, tulip, onion, cabbage, potato, pea, lentil, apricot, cherry, onion, maple tree, basswood tree, boxelder tree, black walnut tree, birch tree, balsam fir, Douglas fir, Eastern white pine and spruce.

25. The method of claim 24 wherein the treated plant is an apple.

26. The method of claim 23 wherein the wax emulsion comprises an edible synthetic oxygen containing wax.

27. The method of claim 23 wherein the plant protective composition comprises about 0.5 to 10% (weight/weight) lipophilic thixotropic smectic clay and about 90 to 99.5% wax emulsion.

28. The method of claim 27 wherein the plant protective composition is diluted into an aqueous solution in a volume/volume ratio of from about 1 part protective coating mixture to about 1 part aqueous solution to about 1 part protective coating mixture to 10 parts aqueous solution.

29. The method of claim 23 wherein the matrix of complex hydrocarbons comprises a wax mixture comprising long chain fatty acids and long chain fatty alcohol esters.

30. The method of claim 29 wherein the wax mixture is a natural wax selected from the group consisting of Carnauba wax, Candelilla wax, Alfa wax, montan wax, rice-bran wax, beeswax, Japan wax and mixtures thereof.

31. The method of claim 23, wherein the plant protective composition is diluted into an aqueous solution prior to treating the plant.

32. The method of claim 23 wherein the plant is treated by spraying the composition onto the surface of the plant.

33. The method of claim 32 wherein the composition is sprayed with an application rate of about 100 to 500 gallons per acre.

34. The method of claim 32 wherein the composition is sprayed onto the plant multiple times.

* * * * *